(12) United States Patent
Linehan

(10) Patent No.: US 6,855,150 B1
(45) Date of Patent: *Feb. 15, 2005

(54) PATELLAR TRIAL AND DRILL GUIDE FOR USE IN KNEE REPLACEMENT SURGERY

(76) Inventor: Timothy R. Linehan, 5548 Point Dr., West Bend, WI (US) 53095

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/904,942

(22) Filed: Jul. 13, 2001

(51) Int. Cl.$^7$ .............................................. A61B 17/58
(52) U.S. Cl. .......................................... 606/96; 623/20
(58) Field of Search .............................. 606/96, 88, 87; 623/20.14, 20.18, 20.19, 20.2, 20.15, 20.42, 23.11

(56) References Cited

U.S. PATENT DOCUMENTS

| | | | |
|---|---|---|---|
| 4,565,192 A | | 1/1986 | Shapiro ........................ 128/92 |
| 4,706,660 A | * | 11/1987 | Petersen ....................... 606/86 |
| 5,030,219 A | * | 7/1991 | Matsen et al. ................. 606/53 |
| 5,035,700 A | * | 7/1991 | Kenna ........................... 606/87 |
| 5,129,908 A | | 7/1992 | Petersen ........................ 606/88 |
| 5,380,332 A | | 1/1995 | Ferrante ........................ 606/80 |
| 5,383,937 A | * | 1/1995 | Mikhail ..................... 623/20.18 |
| 5,480,443 A | * | 1/1996 | Elias .......................... 623/20.18 |
| 5,486,177 A | | 1/1996 | Mumme et al. ............... 686/79 |
| 5,520,692 A | | 5/1996 | Ferrante ........................ 606/79 |
| 5,536,271 A | | 7/1996 | Daly et al. ..................... 606/80 |
| 5,542,947 A | | 8/1996 | Treacy ........................... 606/88 |
| 5,571,196 A | * | 11/1996 | Stein ......................... 623/20.19 |
| 5,571,197 A | | 11/1996 | Insall ........................... 623/20 |
| 5,575,793 A | | 11/1996 | Carls et al. .................... 606/80 |

(List continued on next page.)

OTHER PUBLICATIONS

"Surgical Techniques for Preparation of the Patella Using the Zimmer Patella Reamer"; Zimmer, Inc. 1990, 1991.
"NexGen Sytem Complete Knee Solution; Implant Options; The System of Specifics"; Zimmer, Inc. 1998.
"NexGen System Complete Knee Solution; Instrumentation Options; Surgeon–Specific" Zimmer, Inc. 1998.
"Nexgen Complete Knee Solution; Revision Instrumentation Surgical Technique for Legacy Constrained Condylar Knee"; Zimmer, Inc. 1997, 1999.
"Nexgen Complete Knee Solution; Surgical Technique for Cruciate Retaining Knees" Zimmer, Inc. 1995.

*Primary Examiner*—Michael Milano
*Assistant Examiner*—Victor Nguyen
(74) *Attorney, Agent, or Firm*—Godfrey & Kahn, S.C.

(57) ABSTRACT

A patellar trial and drill guide for use during knee replacement surgery comprising an articular surface member and a fixation peg drill guide. The articular surface member is the exact geometry as the artificial patellar implant, and the drill guide aligns the holes for the fixation pegs of the artificial patellar implant. The patellar trial is placed on the resected patella in the desired position, a patellar clamp is used to temporary fix the patellar trial to the patella. The patella is then returned to its normal position and a trial reduction of the total knee replacement is completed. If the placement and/or size of the patellar trial is unacceptable, the patella is inverted, the patellar trial removed, and a different sized trial or new location is determined. The new patellar trial is secured to the resected patella, and another trial reduction of the total knee replacement is completed. This procedure can be repeated until the patellar trial is the correct size and in the proper location. If the placement of the patella is acceptable, the patella is inverted, the articular surface member removed, fixation peg holes are drilled using the fixation peg holes of the drill guide, and an artificial patellar implant is implanted on the patient's remaining patella.

14 Claims, 6 Drawing Sheets

U.S. PATENT DOCUMENTS

| | | | |
|---|---|---|---|
| 5,580,353 A | 12/1996 | Mendes et al. | 623/20 |
| 5,667,512 A | 9/1997 | Johnson | 623/21 |
| 5,690,637 A | 11/1997 | Wen et al. | 606/88 |
| 5,702,465 A * | 12/1997 | Burkinshaw | 623/20.2 |
| 5,716,360 A | 2/1998 | Baldwin et al. | 606/80 |
| 5,769,856 A * | 6/1998 | Dong et al. | 606/96 |
| 5,824,099 A | 10/1998 | Mendes et al. | 623/20 |
| 5,871,540 A * | 2/1999 | Weissman et al. | 623/20.18 |
| 5,941,884 A | 8/1999 | Corvelli et al. | 606/88 |
| 6,010,509 A * | 1/2000 | Delgado et al. | 606/87 |
| 6,056,756 A | 5/2000 | Eng et al. | 606/87 |
| 6,080,196 A | 6/2000 | Bertin | 623/20.14 |
| 6,159,246 A | 12/2000 | Mendes et al. | 623/20 |
| 6,174,314 B1 | 1/2001 | Waddell | 606/88 |
| 6,217,617 B1 * | 4/2001 | Bonutti | 623/20.14 |

* cited by examiner

PATELLAR TRIAL AND DRILL GUIDE FOR USE IN KNEE REPLACEMENT SURGERY

BACKGROUND OF THE INVENTION

The present invention relates to a surgical technique and instrumentation for the placement, trial, and fixation of an artificial patellar component in primary total knee replacement or revision total knee replacement surgery. Specifically, the present invention relates to a patellar trial consisting of an articular surface member and a fixation peg drill guide for use during knee replacement surgery. The invention can easily be adapted to any patellar component and any fixation method.

The patellar trial and drill guide of the present invention can be used during all surgical techniques for trialing a patellar component prior to establishing fixation peg holes, fixation crosses, or fixation rings during knee replacement surgery. These techniques may include modifying a patellar trial so it can be temporarily fixed to a resected patella, performing a trial reduction with the patellar trial in place, marking the placement of a patellar trial on the patella to aid in using a drill guide for establishing fixation peg holes, and using a patellar trial as a x-ray marker or guide to aid in the placement of artificial replacement implants.

The patella, commonly called the kneecap is the part of the human skeleton that articulates with the femur. The articular surface of the patella is held in place against the distal femur the femoral condyles by the patella tendon. The patella provides the leverage necessary for proper functioning of the knee joint. If the articular surface of the patella decays, or is degenerated, proper functioning of the knee joint is not possible with the constant pain and immobility typically associated with these conditions.

Joint replacement is becoming increasingly widespread. One of the most widely practiced joint replacements involves the knee joint. In many cases, the replacement of the knee joint with prosthesis also involves the replacement of a portion of the patella with a prosthetic implant.

The leading cause of clinical failure of primary total knee replacement, or revision total knee replacement surgeries is patella problems, such as pain and dysfunction of the patella femoral joint. Many patella failures are related to patella misalignment and tracking with the femoral and tibial replacement components and with the knee extensor mechanism. When the patella fails, it frequently cannot be satisfactorily resurfaced, leading to either removal of its components or a patellectomy. These procedures often result in a major compromise to the functioning knee.

Another factor in determining ultimate patella tracking and prosthesis longevity is accurate placement of the patellar prosthesis in the knee. The patella's articulation with the femoral groove and femoral component is especially integral to the longevity and success of the prosthesis.

One method popularized as a way to increase patellar prosthesis longevity is lateral retinacular release. Lateral retinacular release is used to improve patella tracking when the prosthesis does not track properly after is has been surgically implanted. However, several problems associated with lateral retinacular release are well known including increased post-operative hemarthrosis and hematoma. Extensive lateral retinacular release also increases the probability of a vascular necrosis due to the sacrifice of the patellar branch of the superior lateral geniculate artery.

Presently there is no method for trialing a patellar implant before permanent location of the patellar implant is determined and committed to. Also there are no techniques or instrumentation for trialing patellar implants of different thicknesses or diameters. Trialing patella's of different thicknesses or diameters is especially crucial in total knee revision surgery.

The tools available to the surgeon also influence the success of surgical techniques in total knee replacement surgery, and patella longevity. Presently, suitable instrumentation systems and cutting guides for the tibial and femoral components are known in the art. These systems and tools have improved surgeon's abilities to implant the components properly and have reduced failures due to improper tibial and femoral component alignment.

However, there are no known prior art teachings of methods or tools that take into consideration the position of the patella in relation to the trial femur and tibial component before committing to the location of the patellar component.

Existing instrumentation for patellar implant trial and fixation include a series of patellar trials ranging is diameters from approximately 26 mm to approximately 48 mm in 2 to 3 mm increments, a series of fixation peg drill guides of the same diameters, a stop drill or mill, and a patellar clamp. The patellar trials are the exact same shape, diameter and thickness as the patellar implants. Some surgical systems have additional instrumentation for resection or removal of unwanted patellar bone.

Present instrumentation and techniques involve guessing on where the patella should be located on the resected patella, holding a drill or mill guide on the patella, preparing the fixation peg holes in the patella, placing the patellar trial on the patella, and performing a trial reduction. It is during the trial reduction that placement and size of the patella is assessed by the surgeon. This assessment should occur before the patellar fixation peg holes have been established, not after.

While performing the trial reduction and assessing the tracking and placement of the patellar trial, if it is determined that a different sized patella is needed, or that moving the patella to a different location is required, the surgeon is very reluctant to make these corrections. Retrialing a patellar implant is rarely done. Moving the location of the patella or trialing a different sized patella requires committing to a new location for the patella, re-drilling the fixation holes in a different location, placing the new trial in the new fixation holes, and then performing another trial reduction.

The reason these corrections are so rarely made is because re-drilling new fixation peg holes in the patella decreases the strength and integrity of the patella, which can lead to patella fracture, necrosis, pain, and ultimately failure of the implant. The results of this reluctance to correct the placement and/or size of the patellar implant are misalignment or improper sizing of the patellar implant. Misalignment or improper sizing of the patellar implant can cause unwanted retinacular releases, patella dislocations, increased polyethylene wear, pain, and ultimately patellar component failure.

Therefore, there remains a need for a method and apparatus of accurately sizing, aligning, trialing, and implantation of patellar components during knee replacement surgeries. Such a technique and instrumentation would decrease total knee replacement failures, specifically due to patella femoral joint misalignments, polyethylene wear, chronic patella dislocation, necrosis, and fracture. The method and apparatus of the present invention satisfies these needs.

SUMMARY OF THE INVENTION

Therefore, in view of the problems associated with the prior instrumentation and methods, it is an objective of the present invention to provide a patellar trial and fixation peg drill guide which overcomes the drawbacks of the prior instruments and techniques.

It is another object of the present invention to provide a patella trial and fixation guide configurable for use with any total knee replacement system. This includes symmetrical and asymmetrical shaped patellae and patellae that use a center fixation peg, two fixation pegs, three fixation pegs, a milled crucifix fixation cross, or a center milled fixation ring.

It is yet another object of the present invention to provide a more accurate method and apparatus for replacing a patella during total knee replacement or revision total knee replacement surgery.

It is still yet another object of the present invention to provide a method and apparatus for allowing surgeons to trial different sized patellar trials having different thicknesses and/or diameters during total knee replacement surgery.

It is a further object of the present invention to provide a method and apparatus that decreases the steps involved in primary total knee replacement or revision total knee replacement surgery, thus, decreasing operative time and potential complications.

It is a still further object of the present invention to provide a method and apparatus for visualizing placement of an artificial patellar implant in relation to the femoral implant before committing to the final placement of the artificial patellar implant.

It is yet a still further object of the present invention to provide a method and apparatus for assessing the placement of an artificial patella using x-ray technology or a pressure sensor.

It is still yet another further object of the present invention to provide a method and apparatus to be used as a x-ray marker during total knee replacement surgery to aid in the placement of the femur, tibia, and/or patellar implants.

The present invention provides a patellar trial and drill guide comprising an articular surface member and a fixation peg drill guide. The articular surface member mates with the fixation peg drill guide of the same size creating the patellar trial and drill guide, which is the exact diameter and thickness of a patellar implant.

The articular surface member is the exact diameter and geometry of the articular surface of the patellar implant. This provides an exact replication of the patella femoral interface and the properties associated with articulation between the two implants. the articular surface member includes a rounded or domed-shaped top surface, a substantially flat bottom surface, and a plurality of pegs extending outwardly and downwardly from the bottom surface. The pegs coincide and mate with a plurality of peg holes extending through the fixation peg drill guide. These pegs are slightly shorter then the thickness of the fixation peg drill guide and slightly shorter in diameter then the diameter of the peg holes to provides for a tight interface between the two components, and allow the patellar trial and drill guide to sit flush on a resected patella. The articular surface member pegs also include fixation pins extending outwardly and downwardly from the bottom center of the pegs. These fixation pins help to temporarily fixate the patellar trial to the resected surface of the patella during surgery.

The fixation peg drill guide acts as the base of the articular surface member. The fixation peg drill guide preferably has a circular shape with a given thickness, a substantially flat top surface and a substantially flat bottom surface. The fixation peg drill guide further includes a plurality of peg holes extending therethrough for mating with the pegs of the articular surface member. A plurality of fixation pins extend outwardly and downwardly from the bottom surface of the fixation peg drill guide at various locations around the plurality of peg holes. These fixation pins are used to temporarily fixate the fixation peg drill guide to the patella.

The present invention also contemplates the method for using the patellar trial and drill guide during primary total knee replacement or revision total knee replacement surgery. The patellar trial and drill guide is used for determining the proper location, size, and thickness of a permanent artificial patellar implant during surgery. The patella is resected in the normal fashion, this is usually completed after the femoral and tibial components have been seated, trialed, and assessed. Resection of the patella involves inverting the patella and removing bone from the underside of the patella. This is the surface of the patella that articulates with the femur. The patellar trial and drill guide is placed on the resected patella. The patellar trial and drill guide is then temporarily secured to the patella using a patellar clamp. Trial reduction is performed by the surgeon. If it is determined that a different patellar trial is needed or that its location should be changed, the patellar trial and drill guide is removed and/or replaced with a different sized patellar trial and/or moved to a different location on the patella. Another trial reduction is performed by the surgeon using the new and/or relocated patellar trial and drill guide. If the patellar trial and drill guide is the proper size and in the proper location, the surgeon will prepare the patella to receive the artificial patellar implant. With the patellar trial and drill guide still secured to the patella, the articular surface member is separated and removed from the fixation peg drill guide and a patellar drill is used to create fixation peg holes in the patella. The patellar implant is then implanted and secured to the resected patella by inserting and securing fixation pegs of the implant into the fixation peg holes drilled into the patella.

The advantages of the present invention are that the invention allows a surgeon to trial an artificial patellar implant before drilling the fixation peg holes in the patient's natural patella. The present invention also provides the surgeon with the opportunity to perform a trial reduction with all the trial implants in their desired locations. Having this opportunity enables the surgeon to accurately assess patellar tracking, location, thickness and diameter, in relation to the femoral and tibial components. Stresses between the patellar trial and femoral component can be monitored and assessed during the entire range of motion of the knee joint. The ability to monitor how the patella tracks prior to implanting the components increases the likelihood of long term total knee replacement success. It also provides the opportunity to move the patellar trial to a more desirable location, or choose a different size, diameter or thickness patella, if it is determined to be needed by the surgeon. This can be completed without having to re-drill new patellar fixation peg holes. In addition, the surgeon can view the placement of the patellar trial by taking a x-ray of the implants.

Various other features, objects, and advantages of the invention will be made apparent to those skilled in the art from the accompanying drawings and detailed description thereof.

DETAILED DESCRIPTION OF THE INVENTION

Figure 1:
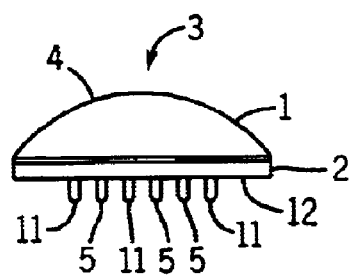
FIG. 1 is a side view of a patellar trial and drill guide in accordance with the present invention.
Figure 2:
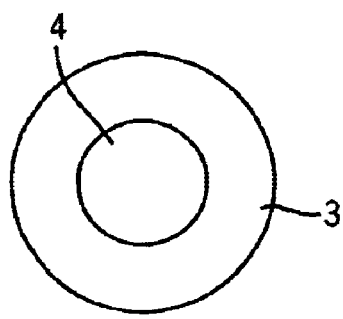
FIG. 2 is a top view of the patellar trial and drill guide of FIG. 1.
Figure 3:
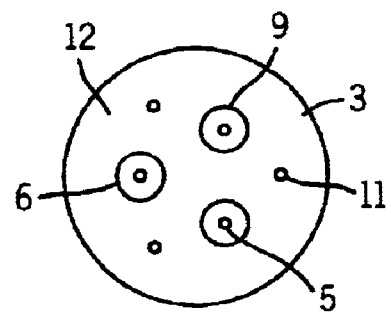
FIG. 3 is the bottom view of the patellar trial and drill guide of FIG. 1.

Referring now to the drawings, FIGS. 1–4 illustrate the patellar trial and drill guide 3 of the present invention. A patellar trial is used during primary total knee replacement surgery or revision total knee replacement surgery to assess the placement and function of the patella and femur. The correct articulation between the patella and femur is crucial to long term success of total knee replacement surgery.

To surgically replace a damaged patella, the damaged portions of the natural patella articulating surface are removed or resected, while preserving as much of the natural patella bone as possible and leaving the attachments between the natural patella, the muscle and the tendon intact. The resection should be as flat and straight as possible to insure a secure bond with a patellar implant. An artificial patellar implant is then attached to the resected surface of the natural patella. During this process, a patellar trial is used to determine the exact size, shape and location of the patellar implant. The patellar implant articulates with the femoral groove of the femoral implant. The present invention provides an improved patellar trial and drill guide 3 for use in determining the exact size, shape and location of a patellar implant during knee replacement surgery.

The patellar trial and drill guide 3 of the present invention comprises two components, an articular surface member 1 and a fixation peg drill guide 2. The fixation peg drill guide 2 acts as the base of the articular surface member 1. The patellar trial and drill guide 3 is the exact design, diameter and thickness as an actual artificial patellar implant. Using a patellar trial is essential in determining the accurate placement and size of the actual patellar implant. Patellar trials typically range in size from 25 mm to 49 mm in diameter and 7 mm to 10 mm thick. The diameter of the patellar trials vary, increasing by 2 to 3 mm. As the diameters increase, the thickness of the patellar trials also increase by approximately 0.5 mm for each 2 to 3 mm increase in diameter. The patellar trial and drill guide 3 of the present invention, including the articular surface member 1 and a fixation peg drill guide 2 are, thus, also available in the same diameters and thicknesses as the patellar trials.

The patellar trial and drill guide 3 includes a rounded or domed-shaped top surface 4 and a substantially flat bottom surface 12 with a plurality of pins 5, 11 extending downwardly therefrom. These pins 5, 11 are used to temporarily fixate the patellar trial and drill guide 3 to the resected surface of a patient's patella.

Figure 14:
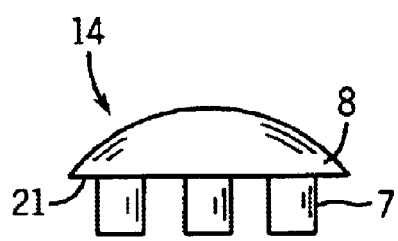
FIG. 14 is a side view of a patellar implant for implanting onto the resected patella.

The articular surface member 1 is the exact geometry and diameter of the articular surface 8 of the patellar implant 14, as shown in FIG. 14. This provides an exact replication of the patella femoral interface and the properties associated with articulation between the two implants. The articular surface member 1 mates with the fixation peg drill guide 2 of the same diameter creating the patellar trial and drill guide 3, which is the exact diameter and thickness of the patellar implant 14.

Figure 4:
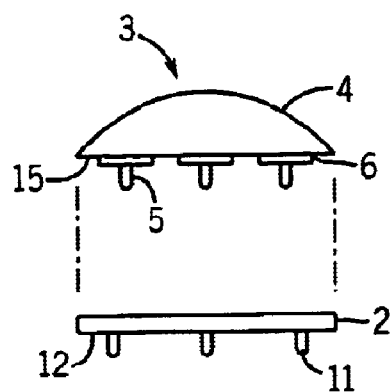
FIG. 4 is an exploded view of the patellar trial and drill guide of FIG. 1.
Figure 5:
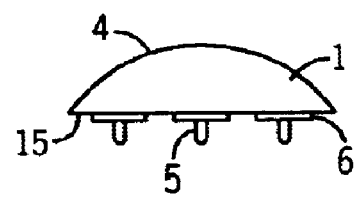
FIG. 5 is a side view of an articular surface member of the patellar trial and drill guide of FIG. 1.

As is best shown in FIGS. 4 and 5, the articular surface member 1 includes a rounded or domed-shaped top surface 4, a substantially flat bottom surface 15, and a plurality of pegs 6 extending outwardly and downwardly from the bottom surface 15 of the articular surface member 1. These pegs 6 coincide and mate with a plurality of peg holes 9 extending through the fixation peg drill guide 2. These pegs 6 are approximately 0.05 mm shorter then the thickness of the fixation peg drill guide 2 and approximately 0.05 mm shorter in diameter then the diameter of the peg holes 9. This provides for a tight interface between the two components, and allows the patellar trial and drill guide 3 to sit flush on the resected patella. The articular surface member pegs 6 also include fixation pins 5 extending outwardly and downwardly from the center of the bottom of the pegs 6. These fixation pins 5 help to temporarily fixate the patellar trial 3 to the resected surface of the patella. The fixation peg drill guide 2 also includes a plurality of fixation pins 11 extending outwardly and downwardly from the bottom surface 12 of the fixation peg drill guide 2.

Figure 6:
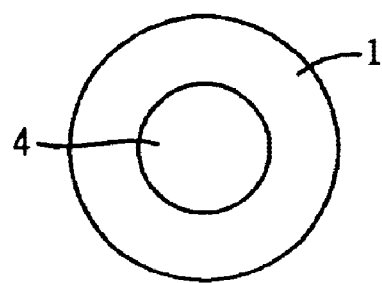
FIG. 6 is a top view of the articular surface member of FIG. 5.
Figure 7:
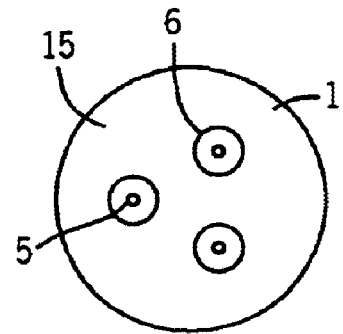
FIG. 7 is a bottom view of the articular surface member of FIG. 5.

Referring next to FIGS. 5–7, the articular surface member 1 is preferably circular in shape with a rounded or domed-shaped top surface 4 and a substantially flat bottom surface 15. As mentioned previously, a plurality of pegs 6 extend outwardly and downwardly from the bottom surface 15 of the articular surface member 1. The pegs extend approximately 0.95 mm from the bottom surface 15 of the articular surface member 1 and are approximately 6 mm in diameter. In the most preferred embodiment, there are preferably two pegs 6 on the lateral side on the bottom surface 15 of the articular surface member 1 and one peg 6 on the medial side on the bottom surface 15 of the articular surface member 1. The pegs 6 are preferably circular in shape, with the centers of the pegs being approximately 1 cm from the edge of the articular surface member 1. The pegs 6 are preferably arranged in a triangle design with pegs at the 12, 4, and 8 o'clock positions. The pegs 6 include fixation pins 5 extending outwardly and downwardly from the center of the bottom of the pegs 6. The fixation pins 5 are approximately 1 to 3 mm in length and approximately 1 mm in diameter. The fixation pins 5 are used to temporarily fixate the articular surface member 1 to the patella. The fixation pins 5 are preferably molded as part of the articular surface member 1, and come to a sharp point. The material used in manufacturing the articular surface member 1 should be the same as used for standard patellar trials and implants. The diameter of the articular surface member 1 is preferably marked on the bottom surface 15 of the articular surface member 1. The same diameter articular surface member 1 and fixation peg drill guide 2 must be used to make the proper sized patellar trial and drill guide 3.

Figure 8:
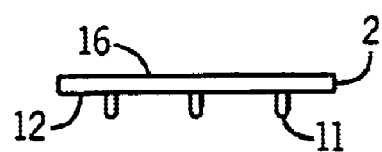
FIG. 8 is a side view of a fixation peg drill guide of the patellar trial and drill guide of FIG. 1.
Figure 9:
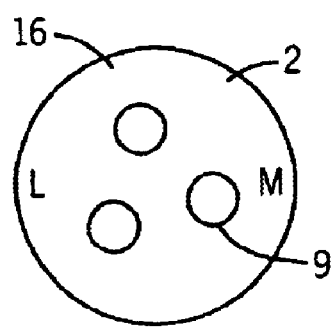
FIG. 9 is a top view of the fixation peg drill guide of FIG. 8.
Figure 10:
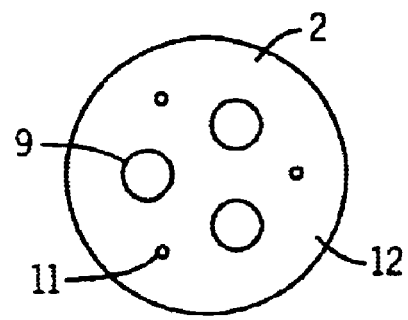
FIG. 10 is a bottom view of the fixation peg drill guide of FIG. 8.

Referring next to FIGS. 8–10, fixation peg drill guide 2 is shown with a circular shape having a substantially flat top surface 16 and a substantially flat bottom surface 12. The thickness of the fixation peg drill guide 2 is approximately 1 mm and is the same for all available diameters. The fixation peg drill guide 2 includes a plurality of peg holes 9 extending through the fixation peg drill guide 2. There are preferably two holes 9 on the lateral side of the guide 2 and one hole 9 on the medial side of the guide 2. The peg holes 9 are preferably circular in shape and are approximately 6 mm in diameter, with the centers of the holes being approximately 1 cm from the edge of the fixation peg drill guide 2. The peg holes 9 are preferably arranged in a triangle design with holes at the 12, 4, and 8 o'clock positions. A plurality of fixation pins 11 extend outwardly and downwardly from the bottom surface 12 of the fixation peg drill guide 2. The fixation pins 11 are approximately 1 to 3 mm in length and approximately 1 mm in diameter. These fixation pins 11 are used to temporarily fixate the guide 2 to the patella. The pins are preferably made from the same stainless steel material as the fixation peg drill guide 2, but can be made from any rigid or hard material. The fixation pins 11 are preferably located 5 mm from the edge of the fixation peg drill guide and placed symmetrically between the peg holes 9. The fixation pins 11 also preferably number no less then three.

The top surface 16 of the fixation peg drill guide 2 may also include two reference marks L for lateral and M for medial, as shown in FIG. 9. These markings aid the surgeon in placing the guide in the proper location. The diameter of the fixation peg drill guide 2 is also preferably marked on the top and bottom surfaces 16, 12 of the guide 2, so that the correct articular surface member 1 is used in combination with the same diameter fixation peg drill guide 2.

Figure 11:
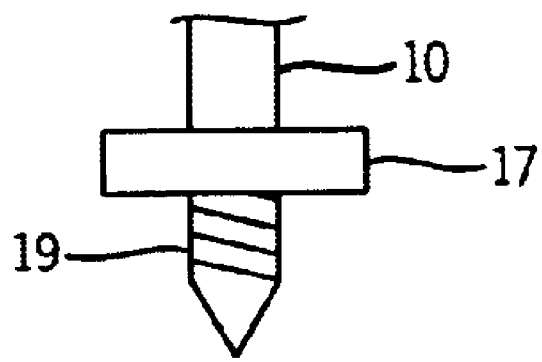
FIG. 11 is a side view of a fixation peg stop drill bit for drilling fixation peg holes in the patella.
Figure 12:
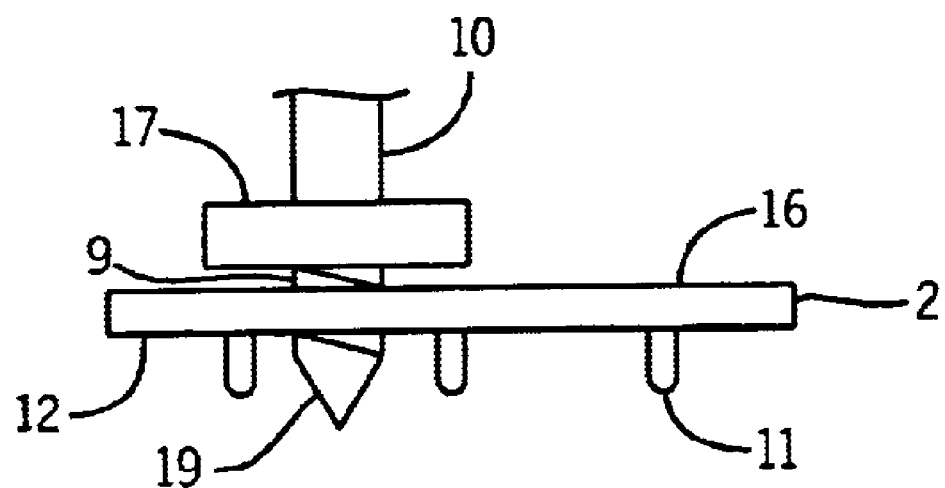
FIG. 12 is a side view of the fixation peg stop drill bit inserted within a drill hole of the fixation peg drill guide.

A fixation peg stop drill bit 10 is shown in FIGS. 11 and 12. The fixation peg stop drill bit 10 is used to drill or mill fixation peg holes in the resected natural patella. FIG. 12 is a side view of the fixation peg stop drill bit 10 inserted within a peg hole 9 of the fixation peg drill guide 2. The bit 19 and stop 17 located on the fixation peg stop drill bit 10 insure that the fixation peg holes 18, FIG. 13, on the patella 20 are all the same diameter and depth. The bit 19 is preferably the same diameter as the peg holes 9 in the fixation peg drill guide 2, and the stop 17 limits the depth of the drill bit 19 into the patella 20 by contacting the top surface 16 of the fixation peg drill guide 2. The fixation peg holes 18 in the patella 20 accept the fixation pegs 7 of the artificial patellar implant 8 and are used to secure and stabilize the artificial patellar implant 8 to the resected natural patella 20.

Figure 13:
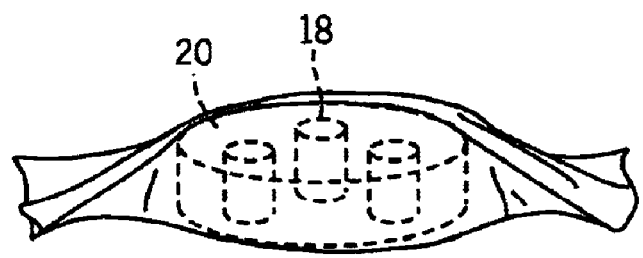
FIG. 13 is a perspective view of a resected patella with three fixation peg holes drilled into the surface of the patella.
Figure 15:
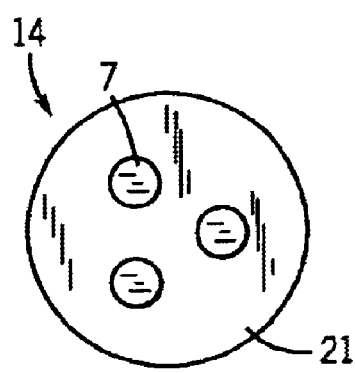
FIG. 15 is a bottom view of the patellar implant of FIG. 14.

FIG. 13 illustrates a resected patella 20 with fixation peg holes 18 extending therein. FIGS. 14 and 15 illustrate an artificial patellar implant 14 with a round or domed-shaped articular surface 8 and a substantially flat bottom surface 21 with a plurality of fixation pegs 7 extending outwardly and downwardly therefrom.

Accommodation of different thickness patellar implants 14 and patellar trials 3 while using only one stop drill bit 10 is done by changing the thickness of the articular surface member 1 proportionately as the thickness of the patellar implant 14 and patellar trial 3 change. The thickness of the fixation peg drill guide 2 remains the same regardless of the thickness of the patellar trial 3 or the patellar implant 14. In the event that an exceptionally thin patellar implant 14 and patellar trial 3 is used, a shorter stop drill bit 10 may be used.

Figure 16:
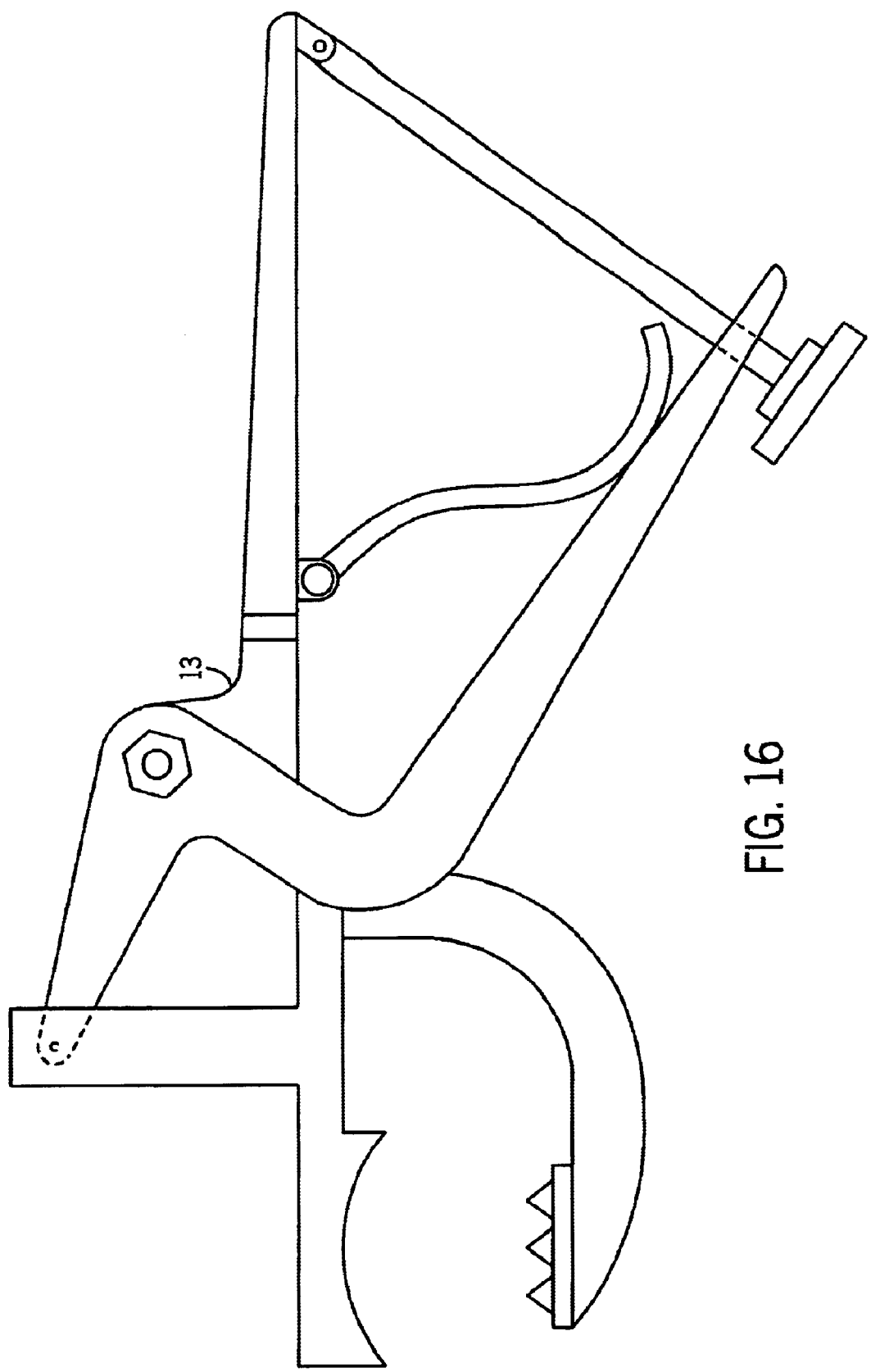
FIG. 16 is a side view of a patellar clamp used for securing the patellar trial to the patella.

FIG. 16 illustrates a patellar clamp 13 that is used during knee replacement surgery to temporarily fixate the patellar trial to the resected patella. The patellar trial is placed on the patella at the desired location, the patellar clamp 13 is then placed over the trial and pressure is applied to the clamp 13. As the patellar trial is being clamped onto the patella the fixation pins are seated into the resected patella, temporarily fixating the patellar trial to the patella. This temporary fixation will allow the patellar trial to stay in place during trial reduction, while not damaging the bone. The pinholes created by the fixation pins can aid in fixation of the artificial patellar implant by serving as fixation anchors for cemented implants or by stimulating bone regeneration in porous implants.

Use of the patellar trial and drill guide 3 of the present invention during primary total knee replacement or revision total knee replacement surgery can be described as follows. First the thickness of the patient's natural patella is measured with a caliber. This is important because the combined thickness of the artificial patellar implant and the remaining patellar bone should be equal to or slightly less than the thickness of the natural patella. It is then determined by the surgeon how much bone is to be resected. Typically, a minimum of approximately 10 mm of patellar bone should be left at all times. Using traditional techniques and instruments the patella is resected to the appropriate thickness. The remaining patellar bone is measured and an appropriate patella size, thickness and diameter is determined. Sizing of the patella is determined by the surgeon based on experience, femoral size, bone thickness and patient anatomy.

After a patella size has been determined the patellar trial and drill guide 3 as seen in FIG. 1, is placed on the patella at the appropriate location. This location is determined by surgeon preference, experience and manufacture recommendations. The patellar trial and drill guide 3 is then temporarily secured to the patella using a patellar clamp 13. The patellar clamp 13 is placed over the patellar trial and drill guide 3 and pressure is applied to the clamp 13 until the patellar trial and drill guide 3 sits flush against the resected patellar bone. It is important that the bottom of the patellar trial and drill guide 3 is flush against the resected patella, as this will insure that the fixation pins 5 and 11 are fully seated, and the patellar trial and drill guide 3 is the same thickness as the artificial patellar implant 14.

The resected patella and patellar trial and drill guide 3 are then returned to their normal positions within the knee joint and a trial reduction is performed by the surgeon. During the trial reduction, the surgeon is assessing flexion and extension of the knee joint, thickness of the tibial articular surface member, patellar tracking, and soft tissue functioning of the patient's knee. It is during the trial reduction that final placement and implant sizing is determined. Intra-operative x-rays may be used to aid in determining the proper location of the patellar trial and drill guide 3. If it is determined that the patellar trial and drill guide 3 is not the appropriate size, diameter or thickness, or is in the wrong location, the surgeon must exchange the patellar trial and drill guide 3, reposition it, or both, and perform another trial reduction.

After determining that a different patellar trial and drill guide 3 or location is needed, the patella is then inverted, and the patellar trial and drill guide 3 removed. A different patellar trial and drill guide 3 is selected, and a new location for the patellar trial and drill guide 3 is determined. To remove the patellar trial and drill guide 3, the surgeon takes a quarter inch osteotome and inserts it between the bottom surface 12 of the drill guide 2 and the resected patella. The osteotome is then used to gently pry loose the patellar trial and drill guide 3 from the bone. The patellar trial and drill guide 3 is then secured in the proper location by the surgeon using the patellar clamp 13.

The patella is returned to its normal position within the knee joint and another trial reduction performed. If the patellar trial and drill guide 3 is the proper size and in the proper location, the surgeon has three options. Verify the location of the patella and other implants with a x-ray, determine patellar tracking and sizing with a patellar sensor, or prepare the patella for receiving an artificial patellar implant 14.

Intra-operative x-rays of the knee with all the trial components in place provide the surgeon with an opportunity to see where the final artificial implants will be, and allows the surgeon to make changes before implanting the components. In addition, the patellar trial and drill guide 3 can be used as a x-ray marker. A patellar x-ray marker is helpful when assessing the joint line and determining where the artificial components should be implanted in relationship to the joint line.

Preparing the patella for the implant 14 is accomplished by removing the articular surface member 1 from the drill guide 2. This is done by inserting a quarter inch osteotome between the articular surface member 1 and the drill guide 2, and gently prying up until the articular surface member 1 can be removed from the drill guide 2. A patellar drill using a stop drill bit 10 is then used to create the fixation peg holes 18 in the patella 20 by drilling through the peg holes 9 in the drill guide 2 until the drill bit stop 17 rests against the top surface 16 of the drill guide 2. The stop 17, drill bit 19 and drill guide 2 insure that the depth and location of the fixation peg holes 18 are the same as the fixation pegs 7 of the patellar implant 14.

After the fixation peg holes 18 are drilled in the patella 20, the patella 20 is now ready to receive the artificial patellar implant 14. The implant 14 is fixed to the resected patella 20 in the normal fashion according to surgeon preference, experience and manufacture recommendations.

This invention is especially beneficial during revision total knee replacement surgery. Having the ability to trial a patella before drilling the fixation holes increases the surgeon's options when replacing the patella and/or femur. Preserving as much patella bone as possible is one of the goals of revision total knee replacement surgery. Having the option to trial a patella without drilling the fixation peg holes provides the surgeon with the option of not sacrificing bone while trialing different size, thickness or shaped patellas. Having the ability to trial a different size, thickness, shape, or material during primary or revision total knee replacement surgery will aid in decreasing patella implant failures, and increase the success rate of both primary and revision total knee replacement surgery.

While the invention has been described with reference to preferred embodiments, those skilled in the art will appreciate that certain substitutions, alterations, and omissions may be made without departing from the spirit of the invention. Accordingly, the foregoing description is meant to be exemplary only and should not limit the scope of the invention set forth in the following claims.

What is claimed is:

1. A patellar trial and drill guide for use in total knee replacement surgery, the patellar trial and drill guide comprising:

an articular surface member having a rounded or domed-shaped top surface and a substantially flat bottom surface with a plurality of pegs extending downwardly and outwardly from the from the bottom surface of the articular surface member;

a fixation peg drill guide for mating with the articular surface member, the fixation peg drill guide having a plurality of openings extending therethrough and coinciding with the plurality of pegs extending downwardly from the bottom surface of the articular surface member;

wherein the articular surface member and the fixation peg drill guide are temporarily fixated to a resected patella for determining the proper location, size, and thickness of a patellar implant; and wherein the articular surface member is separated and removed from the drill guide and the openings in the drill guide are used as a guide for a patellar drill to drill holes in the resected patella for fixating fixation posts of the patellar implant.

2. The patellar trial and drill guide of claim 1 wherein the articular surface member acts as a trial for a patellar implant during total knee replacement surgery.

3. The patellar trial and drill guide of claim 2 wherein the articular surface member is trialed to be the exact diameter and geometry of the articular surface member of the patellar implant.

4. The patellar trial and drill guide of claim 1 wherein the articular surface member articulates with a femoral groove of a femoral implant.

5. The patellar trial and drill guide of claim 1 wherein the pegs mate with the plurality of openings extending through the fixation peg drill guide.

6. The patellar trial and drill guide of claim 1 wherein the pegs include fixation pins extending downwardly and outwardly from the bottom surface of each peg.

7. The patellar trial and drill guide of claim 1 wherein the fixation peg drill guide includes a plurality of fixation pins extending downwardly and outwardly from the bottom surface of the drill guide.

8. A patellar trial and drill guide for use in total knee replacement surgery, the patellar trial and drill guide comprising:

an articular surface member;

a fixation peg drill guide having a plurality of openings extending therethrough;

wherein the articular surface member having a plurality of pegs extending downwardly and outwardly from a bottom surface thereof mates with the fixation peg drill guide and the articular surface member and fixation peg drill guide are temporarily fixated to a resected patella for determining the proper location, size, and thickness of a patellar implant; and wherein the articular surface member is separated and removed from the drill guide and the openings in the drill guide are used as a guide for a patellar drill to drill holes in the resected patella for fixating fixation posts of the patellar implant.

9. The patellar trial and drill guide of claim 8 wherein the articular surface member articulates with a femoral groove of a femoral implant.

10. The patellar trial and drill guide of claim 8 wherein the articular surface member includes a rounded or domed-shaped top surface and substantially flat bottom surface.

11. The patellar trial and drill guide of claim 8 wherein the articular surface member is the exact diameter and geometry of the articular surface member of the patellar implant.

12. The patellar trial and drill guide of claim 8 wherein the articular surface member includes a plurality of pegs extending downwardly and outwardly from the bottom surface, which mate with the plurality of openings extending through the fixation peg drill guide.

13. The patellar trial and drill guide of claim 12 wherein the pegs include fixation pins extending downwardly and outwardly from the bottom surface of each peg.

14. The patellar trial and drill guide of claim 12 wherein the fixation peg drill guide includes a plurality of fixation pins extending downwardly and outwardly from the bottom surface of the drill guide.

* * * * *